United States Patent [19]

Nakazeki et al.

[11] Patent Number: 5,725,357

[45] Date of Patent: Mar. 10, 1998

[54] MAGNETICALLY SUSPENDED TYPE PUMP

[75] Inventors: Tsugito Nakazeki; Hiroyoshi Ito, both of Shizuoka; Teruaki Akamatsu, Kyoto, all of Japan

[73] Assignee: NTN Corporation, Osaka, Japan

[21] Appl. No.: 623,760

[22] Filed: Mar. 29, 1996

[30] Foreign Application Priority Data

Apr. 3, 1995 [JP] Japan ........................ 7-77876
Apr. 14, 1995 [JP] Japan ........................ 7-89260

[51] Int. Cl.$^6$ ........................................ F04B 49/00
[52] U.S. Cl. ...................... 417/18; 417/20; 417/42; 417/43; 417/44.1; 417/44.2; 417/44.3; 417/44.11; 417/423.5; 417/423.12; 415/98; 415/173.5; 415/900
[58] Field of Search ............ 417/18, 20, 22, 417/42, 44.1, 45, 44.2, 44.11, 43, 44.3, 420, 423.5, 423.12, 423.7, 280, 284, 287; 415/98, 101, 173.5, 103, 900

[56] References Cited

U.S. PATENT DOCUMENTS

| | | | |
|---|---|---|---|
| 4,613,281 | 9/1986 | Lubieniecki | 415/98 |
| 4,678,404 | 7/1987 | Lorett et al. | 417/45 |
| 4,732,236 | 3/1988 | Jacques | 415/98 |
| 4,781,525 | 11/1988 | Hubbard et al. | |
| 5,163,818 | 11/1992 | Betsill et al. | 417/22 |
| 5,240,380 | 8/1993 | Mabe | 417/45 |
| 5,350,283 | 9/1994 | Nakazeki et al. | 417/423.7 |
| 5,470,208 | 11/1995 | Kletschka | 417/423.12 |

FOREIGN PATENT DOCUMENTS

| | | | |
|---|---|---|---|
| 0066490 | 3/1989 | Japan | 417/420 |
| 404148095 | 5/1992 | Japan | 417/423.7 |
| 406074184 | 3/1994 | Japan | 417/420 |

*Primary Examiner*—Timothy Thorpe
*Assistant Examiner*—Yuan M. Thai
*Attorney, Agent, or Firm*—Lowe, Price, LeBlanc & Becker

[57] ABSTRACT

In a magnetically suspended type pump, an operating state of the pump can be obtained without using a pressure gauge and a flowmeter. In addition, in the case where the magnetically suspended type pump is applied to a blood pump, in order to reduce the number of connections in a flow path and to avoid thrombus formation, a correlation between current flowing in a motor and flow or a correlation between current flowing in the motor and pressure is obtained in advance, and the speed of rotation of motor is varied by a speed of rotation control circuit in response to an instruction from a CPU circuit, based on the obtained correlation between current and flow or between current and pressure, whereby flow or pressure is controlled.

11 Claims, 11 Drawing Sheets

MAGNETICALLY SUSPENDED TYPE PUMP

BACKGROUND OF THE INVENTION

1. Field of the Invention

The present invention relates to a magnetically suspended type pump. More specifically, the present invention relates to a magnetically suspended type pump which is used for medical instruments such as a blood pump and which calculates pump flow from current and the speed of rotation of a motor for driving an impeller.

2. Description of the Background Art

There are cases where an operating state of a pump is monitored at all times so that an apparatus is operated under optimal conditions, in addition to the case of a blood pump. Indications of an operating state of a pump includes a driving motor input (current and voltage), pressure at an inlet of the pump, output at an outlet thereof, and pump flow.

FIGS. 15 and 16 are diagrams each showing a pump system in which apparatuses for detecting these indications are inserted into a pump circuit. In FIG. 15, although voltage applied to a motor for driving a pump 71, current flowing therein and the speed of rotation thereof can be detected relatively easily, a differential pressure gauge 72 must be connected to both an inlet and an outlet of pump 71 in order to detect pressure, and a flowmeter 73 must be connected to the outlet of pump 71 in order to detect flow.

However, measuring apparatuses such as differential pressure gauge 72 and flowmeter 73 described above are expensive, and the number of connections of circuits such as shown in FIG. 16 is increased, so that thrombus formation is more likely to occur at a stepped portion of the connections if used in a blood pump as an artificial heart. Small clearance, stagnation of blood flow and vortex of flow must be avoided as much as possible in a circuit used for blood.

SUMMARY OF THE INVENTION

It is therefore a primary object of the present invention to provide a magnetically suspended type pump capable of calculating an operating state of the pump without using a pressure gauge and a flowmeter and of reducing the number of connection portions in a circuit when applied to a blood pump so that thrombus formation can be avoided.

In summary, the present invention is a magnetically suspended type pump which supports an impeller by a magnetic bearing and which can be driven by magnetic coupling through a partition therebetween, and in the pump, correlation between motor current and flow or between current and pressure is calculated by an electronic circuit and the speed of rotation of the motor is varied by a driving circuit based on the obtained correlation between current and flow or between current and pressure, whereby flow control or pressure control is carried out.

Consequently, according to the present invention, flow control or pressure control can be achieved without using a pressure gauge or a flowmeter as opposed to a conventional example and the number of connections in a flow path can be reduced, so that thrombus formation can be avoided even if the pump is applied to a blood pump.

In a more preferred embodiment, flow or pressure is corrected according to a value of blood viscosity obtained from disturbance response of the impeller supported by a magnetic bearing. Thus, correction of flow or pressure according to a value of blood viscosity is effective for improvement in accuracy in flow detection.

More preferably, superior sensitivity can be obtained by applying disturbance periodically in order to measure blood viscosity. A frequency of disturbance to be applied is selected to be in the range in which support rigidity of an impeller is smallest.

More preferably, in order to measure blood viscosity, only same frequency as disturbance is passed through a band pass filter.

More preferably, correction according to the speed of rotation is added in order to measure blood viscosity.

More preferably, an impeller has two coaxial blades, and a case includes inlets, outlets and pump chambers which serve as respective flow paths for these two blades. Accordingly, the present embodiment can achieve pumping function of two pumps with a single motor and a single impeller supporting system.

More preferably, these blades are different in shape from each other so that pump chambers have higher pressure and lower pressure at the fixed speed of ration, respectively.

More preferably, the impeller includes circular plates for separating two blades from each other, and the pump has a labyrinth seal structure formed so as to seal space between the circular plate and the case and have diameter increased from the lower pressure side towards the higher pressure side.

The impeller includes a ring-like circular plate provided between the case and the blade located on the lower pressure side for rotating coaxially with the blade, and a self-lubricant provided on the side of inner diameter of the ring-like circular plate for coming in contact with the case when the magnetic bearing malfunctions.

In addition, the magnetic bearing includes a passive type magnetic bearing for radially supporting one side of the impeller, and a control type magnetic bearing for controlling the axial direction of the impeller on the other side. It controls impeller motion about two axis which are at right angles to the axis of rotation.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
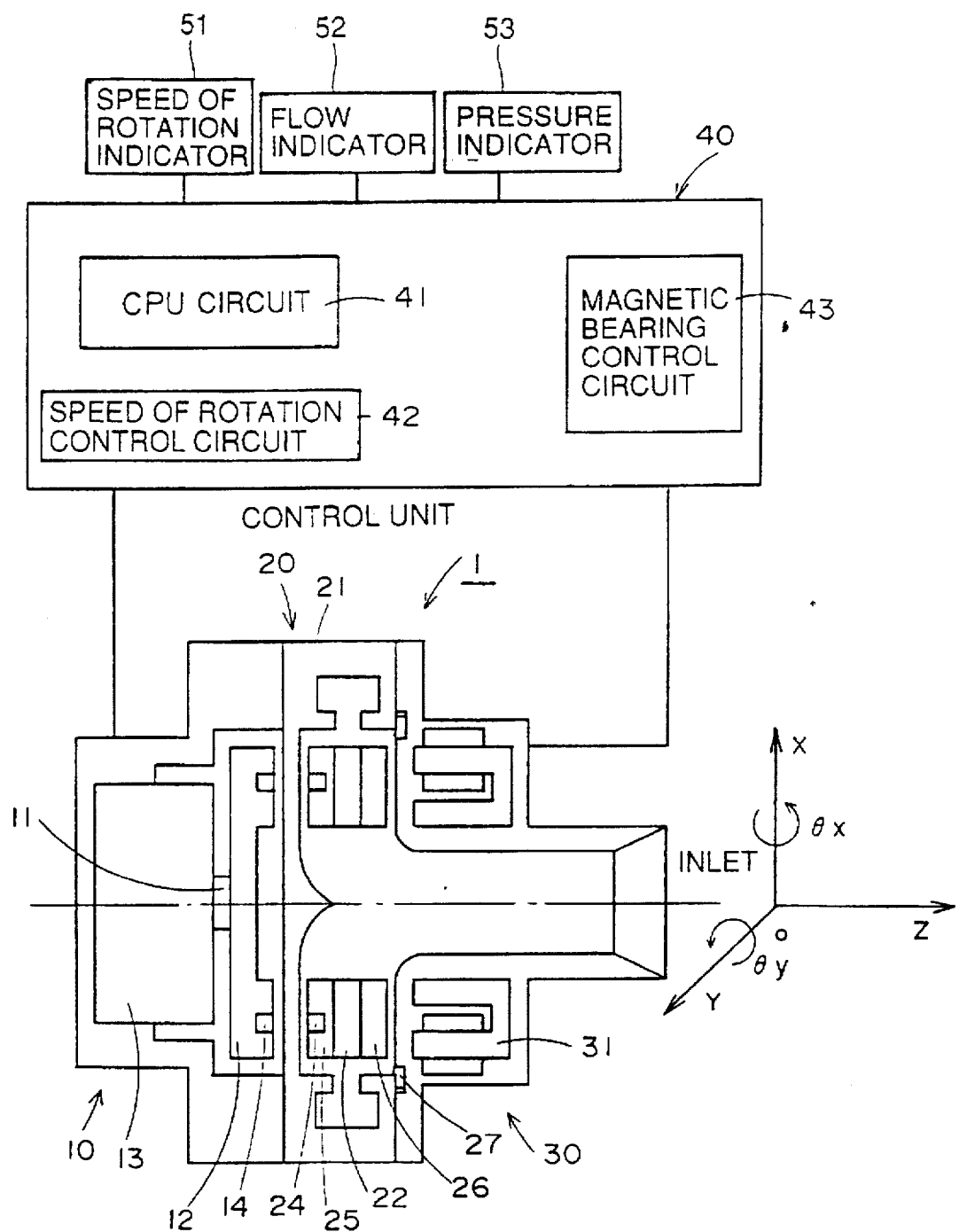
FIG. 1 is a diagram showing a magnetically suspended type pump in a cross section and a control circuit in accordance with one embodiment of the present invention.

FIG. 1 is a diagram showing a magnetically suspended type pump in a cross section and a control circuit in accordance with one embodiment of the present invention. In FIG. 1, a magnetically suspended type pump 1 is constituted by a motor portion 10, a pump portion 20 and a magnetic bearing portion 30. An impeller 22 is provided within a casing 21 of pump portion 20. Casing 21 is formed of a non-magnetic member, and impeller 22 includes a non-magnetic member 25 having a permanent magnet 24 constituting a passive type magnetic bearing, and a soft ion member 26 corresponding to a rotor of a control type magnetic bearing. Permanent magnet 24 is divided in the circumferential direction of impeller 22, and magnets adjacent to each other are polarized in opposite directions.

A rotor 12 supported by a shaft 11 is positioned outside casing 21 so as to be opposite to the side of permanent magnet 24 of impeller 22. Rotor 12 rotates when driven by a motor 13. The same number of permanent magnets 14 as that of magnets 24 located on the side of impeller 22 is provided in rotor 12 so as to be opposite to permanent magnet 24 in impeller 22 and to have attraction. On the other hand, an electromagnet 31 and a position sensor which is not shown are positioned in magnetic bearing portion 30 so as to be opposite to the side of soft iron member 26 of impeller 22 and to overcome the attraction of permanent magnets 24 and 14 in casing 21 to hold impeller 22 in the center of casing 21.

In the magnetically suspended type pump structured as described above, permanent magnet 14 embedded in rotor 12 supports the radial direction and driving of impeller 22, and produces axial attraction between permanent magnet 14 itself and permanent magnet 24 provided in impeller 22. Current is applied to a coil of electromagnet 31 so as to balance with this attraction, and impeller 22 is suspended. Then, if rotor 12 rotates due to the driving force of motor 13, permanent magnets 14 and 24 constitute magnetic coupling and impeller 22 rotates, so that fluid is fed from an inlet port into an outlet port which is not shown. Since impeller 22 is separated from rotor 12 by casing 21 and will not be contaminated by electromagnet 31, blood discharged from magnetically suspended type pump 1 is kept clean.

A control circuit 40 includes a CPU (Central Processing Unit) 41, a rotational speed control circuit 42, and a magnetic bearing control circuit 43. Rotational speed control circuit 42 receives a signal from CPU circuit 41 to control the speed of rotation of motor 13, and magnetic bearing control circuit 43 controls electromagnet 31 based on a signal of the position sensor which is not shown. In addition, control unit 40 includes an indicator 51 for indicating the speed of rotation, an indicator 52 for indicating flow, and an indicator 53 for indicating pressure.

Figure 2:
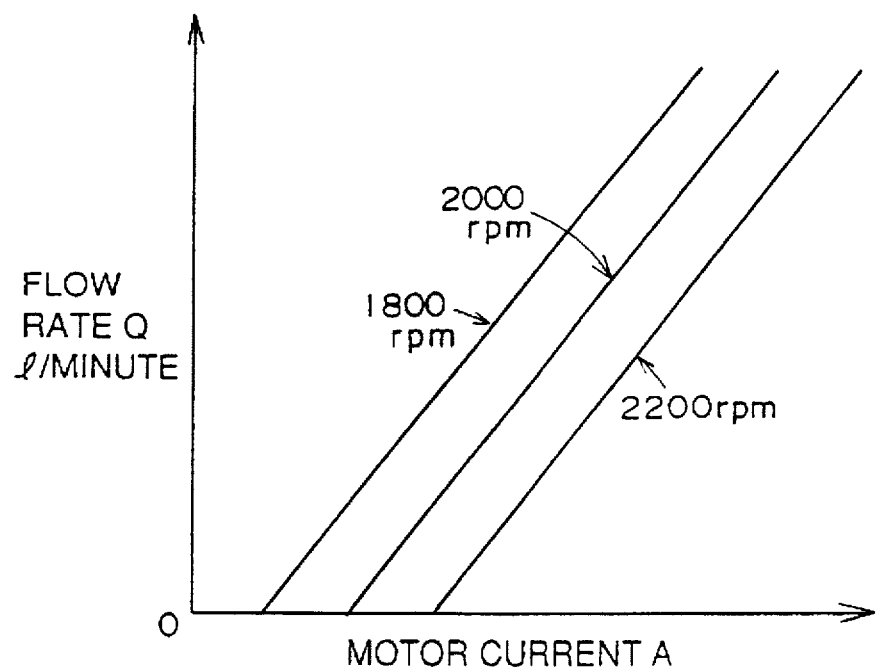
FIG. 2 is a graph showing the relationship between outlet flow of the magnetically suspended type pump and driving current of a motor, which is obtained with the speed of rotation being changed.
Figure 3:
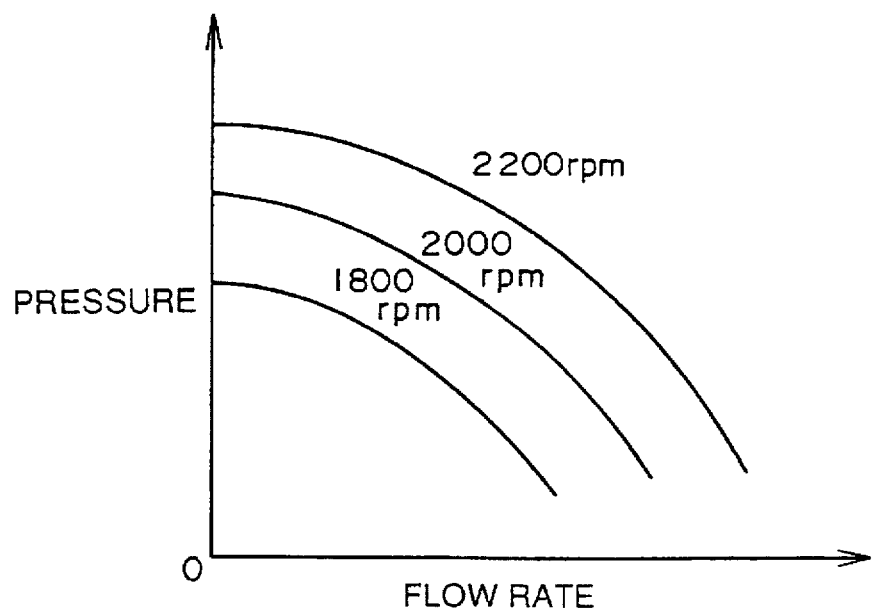
FIG. 3 is a graph showing pump outer flow-pressure characteristics for each speed of rotation.

FIG. 2 is a graph showing the relationship between outlet flow of the magnetically suspended type pump and driving current of the motor, which is obtained with the speed of rotation being changed, and FIG. 3 is a graph showing pump outlet flow-pressure characteristics for each speed of rotation.

Although characteristics of a magnetically suspended type pump change due to clearance between casing 21 and impeller 22 and fluid viscosity, outlet flow can be easily obtained from motor driving current and the speed of rotation as shown in FIG. 2, and further, outlet pressure can be obtained from flow and the speed of rotation as shown in the characteristics of FIG. 3, so long as characteristics are examined in advance for each pump.

Figure 4:
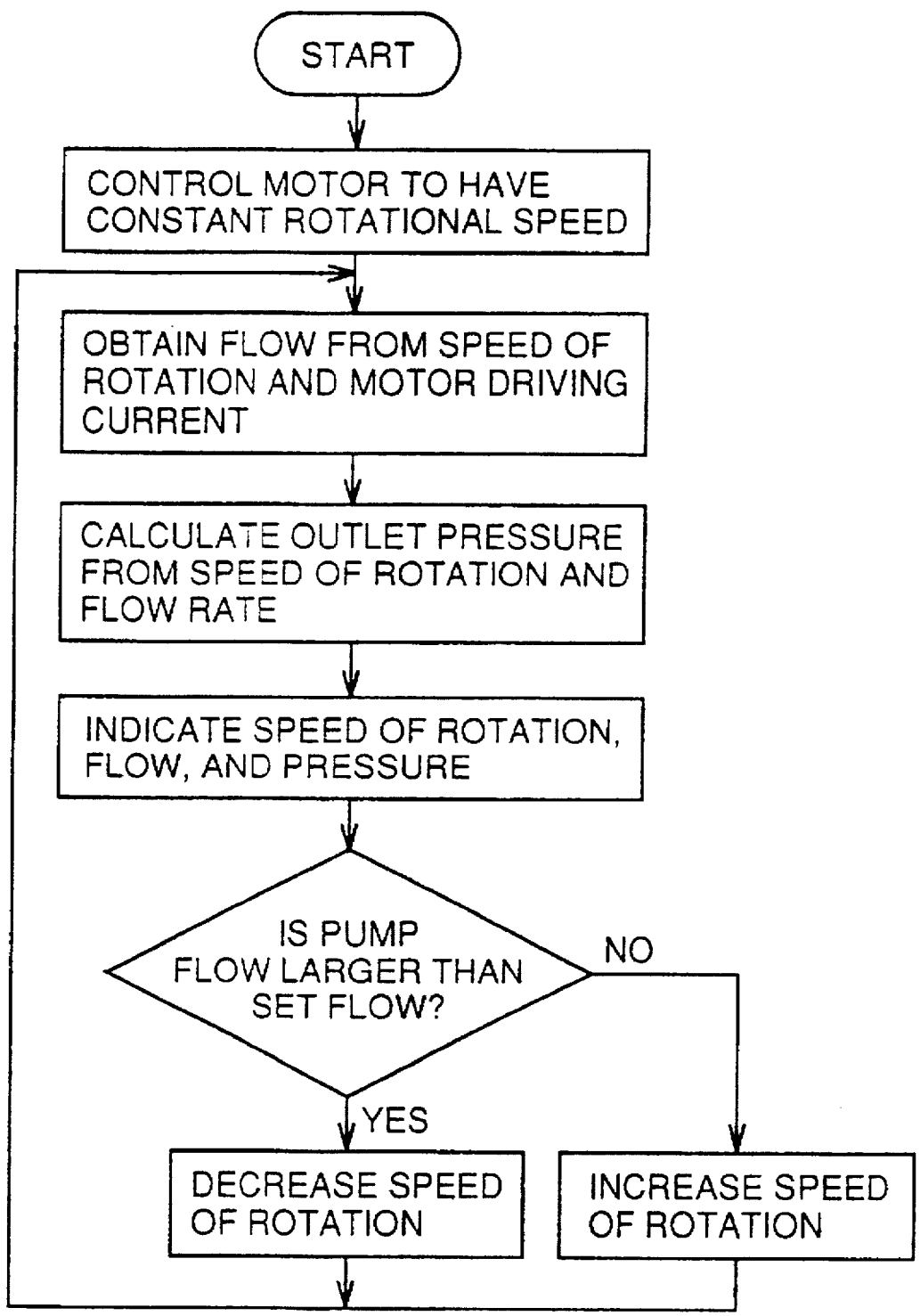
FIG. 4 is a flow chart illustrating the operation of one embodiment of the present invention.

FIG. 4 is a flow chart illustrating the operation of the above described one embodiment of the present invention.

Referring now to FIGS. 1 to 4, specific operation of the present embodiment will be described. The speed of rotation is controlled to be constant by speed of rotation control circuit 42 of control circuit 40. If impeller 22 rotates at a constant speed of rotation of, for example, 2200 rpm, flow can be obtained from the speed of rotation and the motor driving current using the characteristics shown in FIG. 2. In addition, outlet pressure can be obtained from the speed of rotation and the obtained pump flow using the characteristics shown in FIG. 3. In this case, speed of rotation control circuit 42 drives motor 13 based on the signal from CPU circuit 41 so that the speed of rotation of motor 13 is, for example, 2200 rpm. Then, CPU circuit 41 causes indicators 51, 52 and 53 to indicate the speed of rotation, the flow and the discharge pressure, respectively.

Furthermore, in order to control the pump to discharge constant flow, pump flow is obtained from present speed of rotation and present motor driving current and is compared with preset flow, and the speed of rotation is increased if the obtained pump flow is smaller than the preset flow and is decreased otherwise, which is called feed back control. In addition, during operation at a constant outlet pressure, feed back control may be performed with respect to preset pressure.

Consequently, according to the present embodiment, since an operating state of the pump can be obtained without using a pressure gauge and a flowmeter, a magnetically suspended type pump system can be constituted at low cost. Furthermore, if the magnetically suspended type pump system of the present embodiment is applied to a blood pump for artificial heart, the number of connections in a flow path can be reduced, so that thrombus formation can be avoided.

Figure 5:
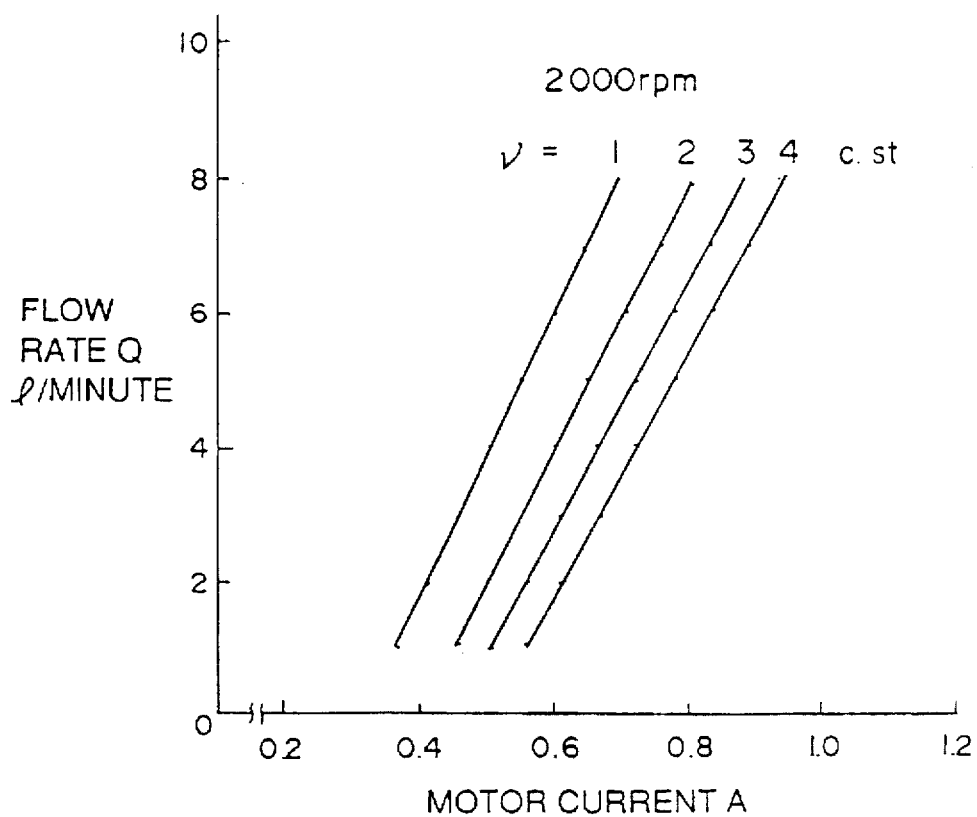
FIG. 5 is a graph showing characteristics of the relationship between motor current and flow, which is obtained at a fixed speed of rotation with viscosity being changed.

FIG. 5 is a graph showing the relationship between motor driving current and flow, which is obtained at a fixed speed of rotation with viscosity being changed. Flow is calculated from the speed of rotation and driving current of motor 13 in the above described embodiment shown in FIG. 1. As shown in FIG. 5, however, even if the speed of rotation is fixed at, for example, 2000 rpm, driving current to achieve constant flow is different depending on blood viscosity, and therefore, change in blood viscosity might result in error. Thus, an embodiment in which flow and pressure are corrected according to blood viscosity will now be described.

Figure 6:
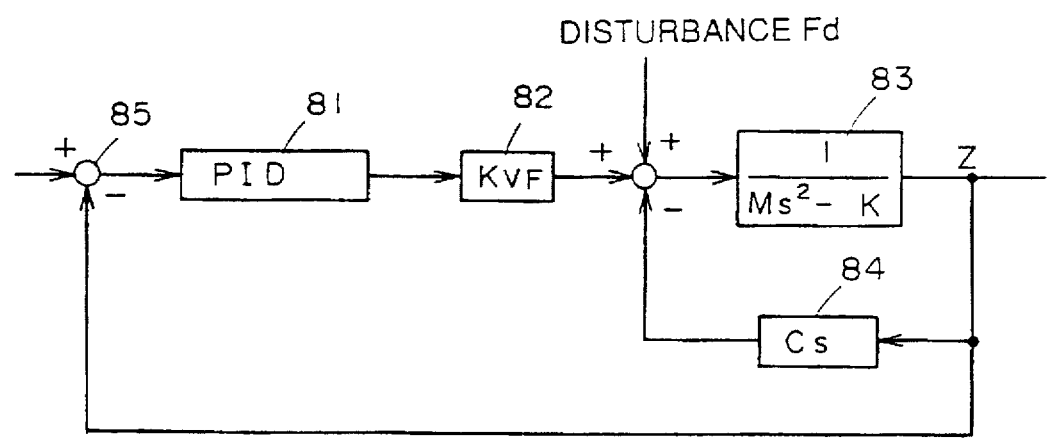
FIG. 6 is a block diagram showing another embodiment of the present invention.

FIG. 6 is a block diagram showing another embodiment of the present invention. A magnetically suspended type pumps has a control loop of three axes Z, $\theta_x$ and $\theta_y$, and each control axis can be shown in a block diagram of FIG. 6. In FIG. 6, a PID (Proportional, Integral and Derivative) circuit 81 is a compensating circuit for stably suspending impeller 22. If a signal with a fixed amplitude and a fixed frequency is added to an output of PID circuit 81, periodic disturbance then acts on impeller 22. In FIG. 6, Cs 84 is force of fluid viscosity. More specifically, if fluid viscosity C changes, displacement of impeller 22 caused by disturbance also varies, and therefore, viscosity can be obtained from the impeller displacement. This method is effective for any one of these three control axes. It is noted that $K_{VF}$ 82 indicates a constant for converting output voltage of PID circuit 81 into coil current, that is, electromagnetic attraction (F), and $1/(M_s^2-K)$ shows a transfer function of controlled system by an electromagnetic bearing.

Figure 7:
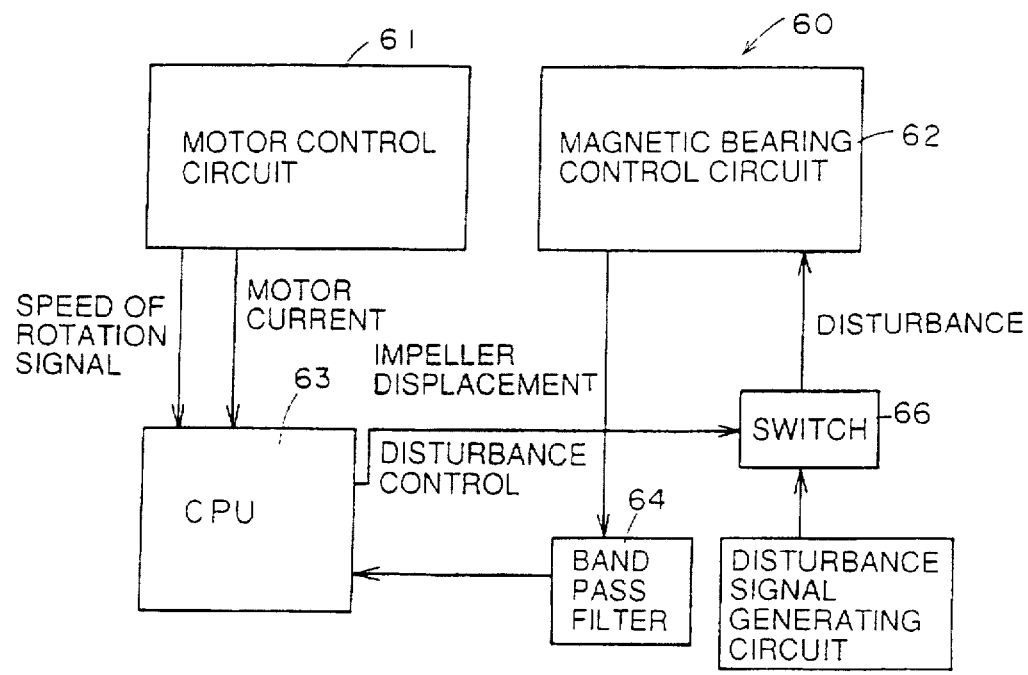
FIG. 7 is a block diagram showing another embodiment of the present invention.

FIG. 7 is a block diagram showing the above described another embodiment of the present invention. In FIG. 7, a control circuit 60 includes a motor control circuit 61, a magnetic bearing control circuit 62, a CPU 63, a band pass filter 64, a disturbance signal generating circuit 65, and a switch 66. A motor driving current value and a signal of the speed of rotation are applied from motor control circuit 61 to CPU 63. CPU 63 calculates flow from the characteristics shown in FIG. 2, based on the speed of rotation signal and the driving current value. A vibration amplitude of an impeller is extracted from magnetic bearing control circuit 62, and is applied to CPU 63 through band pass filter 64. Band pass filter 64 passes impeller vibration signal having the same frequency as that of disturbance, and applies it to CPU 63. In addition, a disturbance signal is generated by disturbance signal generating circuit 65, and disturbance is applied to magnetic bearing control circuit 62 through switch 66. Switch 66 is turned on and off in response to a disturbance control signal from CPU 63.

Figure 8:
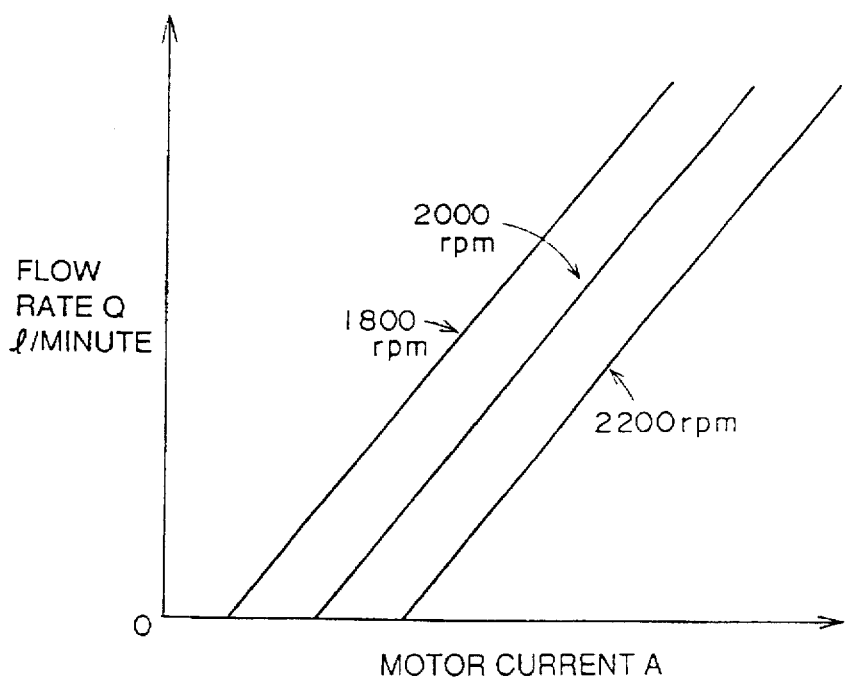
FIG. 8 is a graph showing the relationship between motor driving current and pump flow, which is measured with fixed viscosity.
Figure 9:
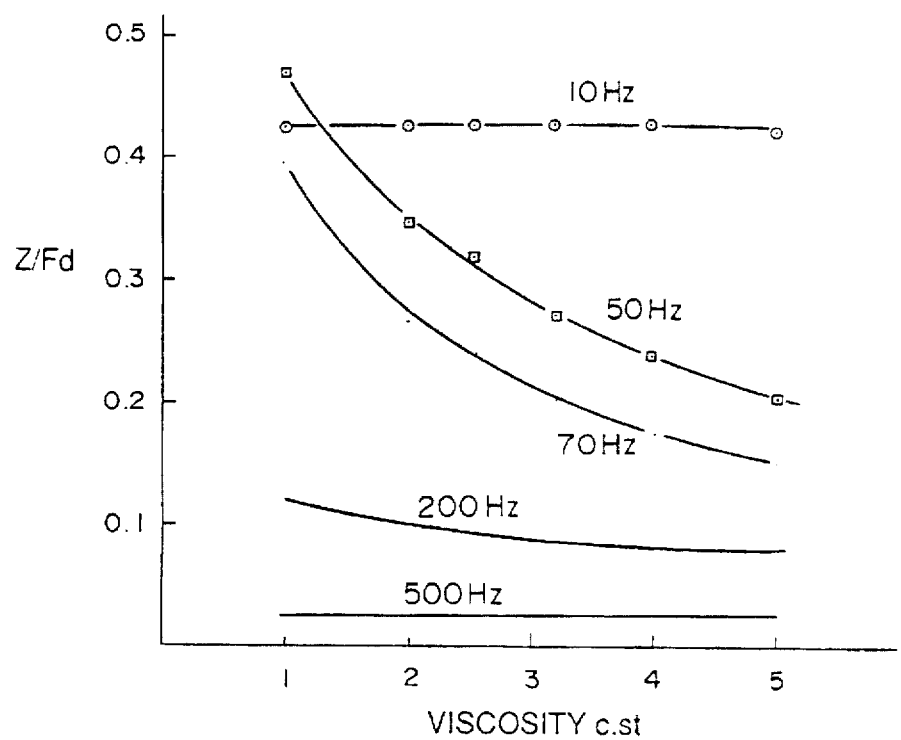
FIG. 9 is a graph showing the relationship between viscosity and displacement of an impeller produced when disturbance having a fixed amplitude is applied thereto in the form of the sin wave, which is obtained with disturbance frequency being changed.
Figure 10:
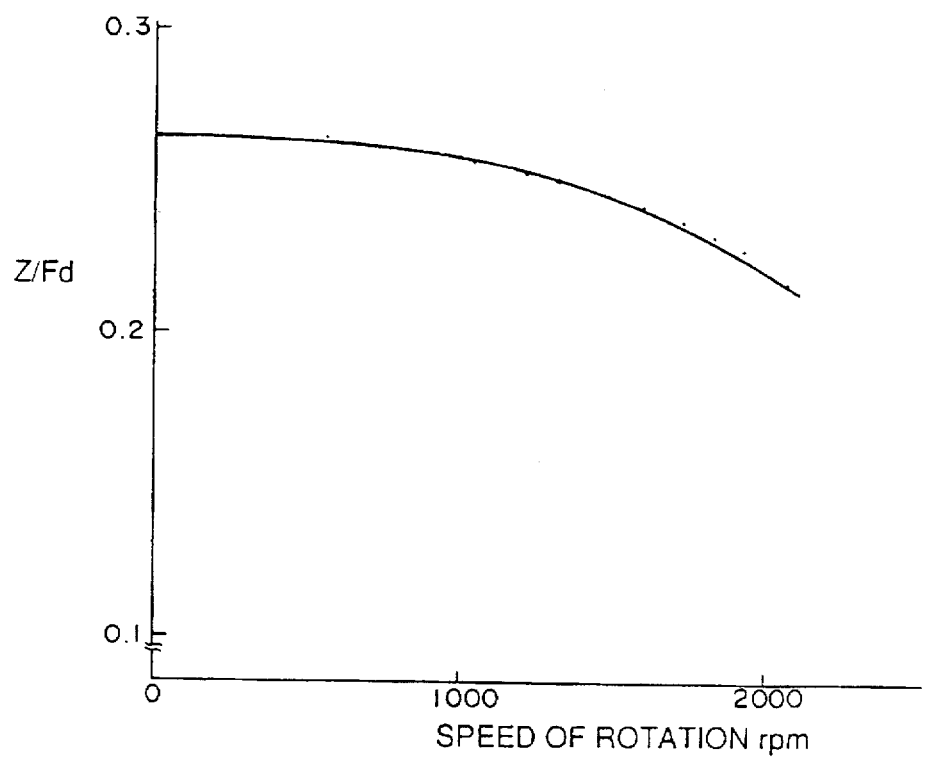
FIG. 10 is a graph showing displacement of the impeller produced when disturbance of 70 Hz is applied thereto, which is measured with the speed of rotation of the impeller being changed.

FIG. 8 is a graph showing the relationship between motor driving current and pump flow, which is obtained with fixed viscosity. FIG. 9 is a graph showing the relationship between viscosity and amplitude (z) of the impeller produced when disturbance (Fd) having a fixed amplitude is applied thereto in the form of the sin wave, which is obtained with disturbance frequency being changed, and FIG. 10 is a graph showing displacement of the impeller with disturbance of 70 Hz, which is measured with the speed of impeller rotation being changed.

As shown in FIG. 5, motor current and pump flow have an approximately linear relationship at fixed viscosity, and CPU 63 calculates flow from the speed of rotation and the motor current value which are applied from motor control circuit 61.

On the other hand, as can be seen from FIG. 9, it is difficult to obtain viscosity from amplitude (z) of the impeller produced when disturbance (Fd) with low frequency or high frequency is applied to the impeller, while superior sensitivity can be obtained for frequency of about 70 Hz (which changes according to setting of a control system) at which impeller support rigidity is smallest. More specifically, it can be understood that fluid viscosity can be obtained using a magnetic bearing. CPU 63 corrects data of FIG. 8 by means of the difference between viscosity during operation which is obtained by the method described above and the standard viscosity which is used to obtain the characteristics of FIG. 8, whereby accuracy in flow detection is improved.

However, if disturbance is applied continuously from disturbance signal generating circuit 65 to magnetic bearing control circuit 62, damage of blood corpuscles (hemolysis) is increased, and therefore, it is desirable to apply disturbance periodically. Accordingly, CPU 63 turns on and off switch 66. In addition, band pass filter 64 extracts impeller displacement having the same frequency as that of disturbance from impeller displacements output from magnetic bearing control circuit 62, and applies the extracted impeller displacement to CPU 63. Furthermore, as shown in FIG. 10, since Z/Fd tends to be reduced as the speed of rotation of the impeller is increased, the speed of rotation must be considered in order to improve accuracy in compensation.

As described above, according to the present embodiment, since correction can be carried out according to blood viscosity, accuracy in flow detection can be improved.

Figure 11B:
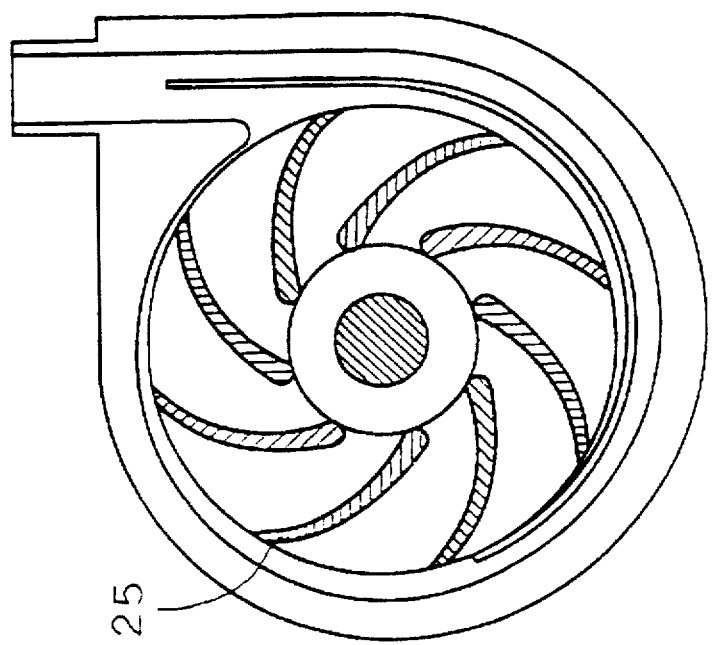
FIGS. 11A and 11B are cross sections showing a further embodiment of a magnetically suspended type pump to which the present invention is applied.
Figure 11A:
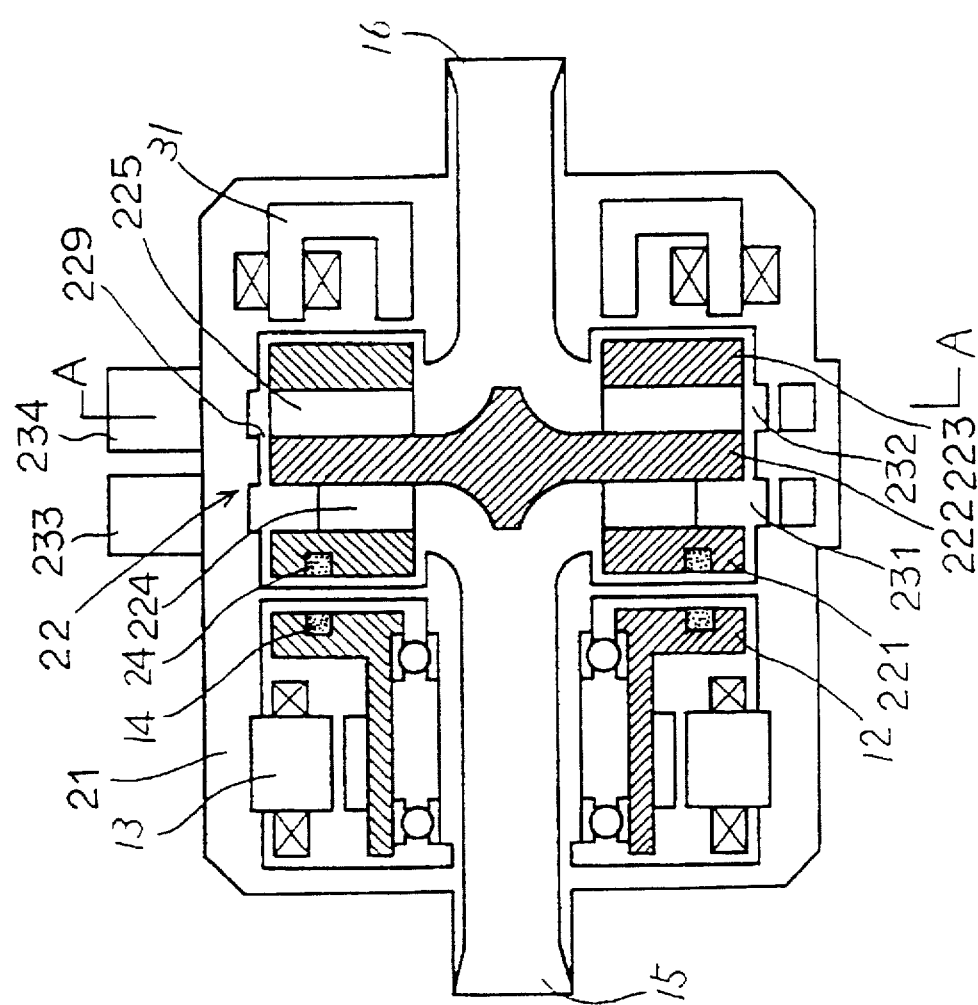

FIGS. 11A and 11B are cross sections showing a further embodiment of a magnetically suspended type pump to which the present invention is applied, wherein FIG. 11A is a longitudinal section of the pump and FIG. 11B is a cross section taken along the line A—A of FIG. 11A. In FIG. 11A, an impeller 22 is constituted by circular plates 221, 222 and 223, and blades 224 and 225 having different diameters and each provided between the circular plates. Each of blades 224 and 225 is formed to have a spiral shape as shown in FIG. 11B. Permanent magnets 24 and 14 are embedded in circular plate 221 and a rotor 12 which is opposite to circular plate 221, respectively, and these permanent magnets 24 and 14 constitute magnetic coupling. Impeller 22 is passively supported by this magnetic coupling. An electromagnet 31 is provided on the side of circular plate 223 as a control type magnetic bearing, and the axial direction of impeller 22, $\theta_x$ and $\theta_y$, are actively supported by electromagnet 31. Then, rotor 12 is rotated when driven by a motor 13, and transmits driving force to impeller 22 by the magnetic coupling.

In addition, an inlet 15 is provided so as to pass through the center of motor 13, and this inlet 15 communicates with an outlet 233 through a pump chamber 231 where blade 224 is rotated. An inlet 16 is further provided so as to pass through the center of electromagnet 31, and this inlet 16 communicates with an outlet 234 through a pump chamber 232 where blade 225 is rotated.

In the magnetic bearing pump shown in FIG. 11A, when impeller 22 is rotated, blade 224 sucks blood returned from the whole body from inlet 15, and supplies the blood through pump chamber 231 from outlet 223 to lungs. On the other hand, blade 225 sucks blood returned from the lungs from inlet 16, and supplies the blood through pump chamber 232 from outlet 234 to the whole body. Required blood flow for a body is determined by controlling the speed of rotation of motor 13 by control circuit 40 shown in FIG. 1. Since flow path of two routes is constituted in the magnetic bearing pump shown in FIGS. 11A and 11B, pumping function of two pumps can be realized with a single magnetic bearing system and a single motor 13. Normally, pressure of blood to lungs is lower than that to the whole body, and flows in lungs and in the whole body are approximately the same. Thus, blades 224 and 225 have different diameters, and blade 224 has smaller diameter than blade 225 in this example.

It is noted that mixture of flows in these two routes at an outer diameter portion 229 of the impeller. In order to avoid this mixture, labyrinth seal as shown in FIGS. 12A—12D is used. More specifically, in FIG. 12A, a projection 235 is provided between pump chambers 231 and 232 in the casing, and a recess 226 is formed at an outer peripheral surface of circular plate 222. However, pressure in pump chamber 232 is higher than that in pump chamber 231 as described above and a shape of clearance on the left side in the figure is the same as that on the right side in the labyrinth seal shown in FIG. 12A, and therefore, fluid force acts on impeller from the side of higher pressure to the side of lower pressure, that is, from right to left in the figure. Accordingly, current flowing in electromagnet 31 is increased in order to hold impeller 22 at a fixed position, and blood leaks from the higher pressure side 232 to the lower pressure side 231.

Figure 12A:
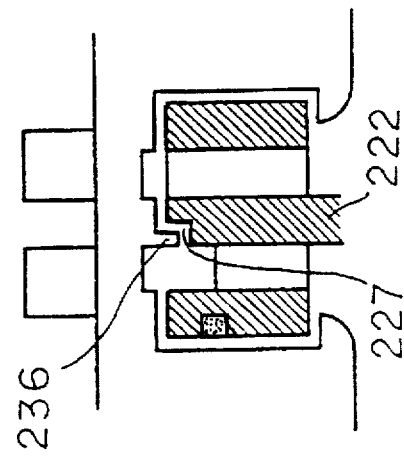
FIGS. 12A–12D are cross sections each showing a main part of labyrinth seal used in an embodiment of the present invention.
Figure 12B:
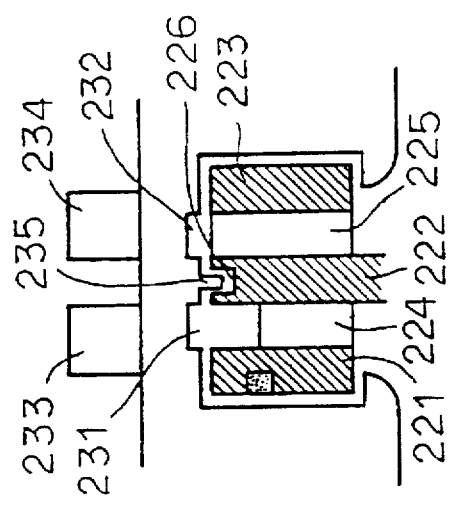
Figure 12C:
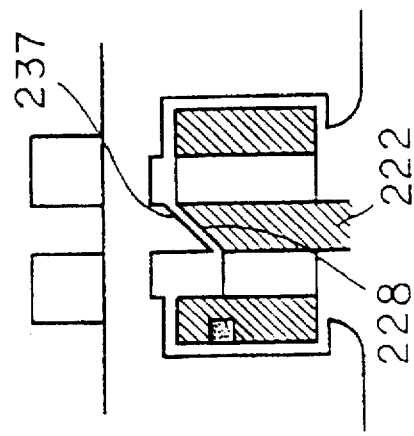
Figure 12D:
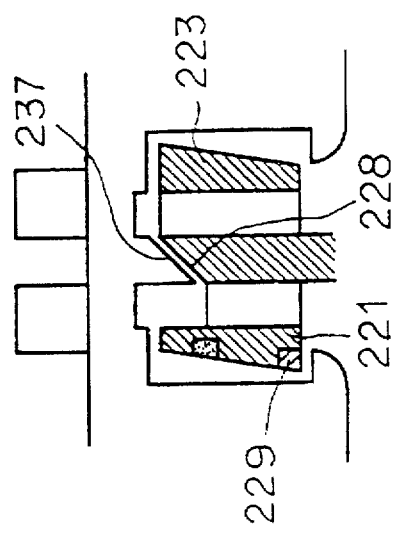

Thus, it is desirable to form labyrinth seal as shown in FIGS. 12B to 12D. More specifically, in the example shown in FIG. 12B, a stepped portion 227 is formed on the side of lower pressure in circular plate 222 and a projection 236 is provided in the casing, and in FIG. 12D, a slope 228 inclined to the side of low pressure is formed at the periphery of circular plate 222 and a slope 237 opposite to slope 228 is formed in the case, whereby sealing property can be improved.

In the labyrinth seal shown in FIG. 12C, slopes are further formed at a surface of circular plate 221 which is opposite to motor 13 and at a surface of circular plate 223 which is opposite to electromagnet 31, respectively, in addition to the example shown in FIG. 12D, so that leftward fluid force is eliminated and current of the electromagnet will not be increased.

By the way, if a magnetic bearing malfunctions and impeller 22 cannot be suspended, impeller 22 comes in contact with the side of the motor due to attraction of magnetic coupling. Thus, a self-lubricant such as a Teflon ring 229 is attached on the side of circular plate 221, whereby stable rotation can be ensured even at the time of malfunction. The same effects can be obtained even if the impeller or the case is coated with the self-lubricant.

Figure 13B:
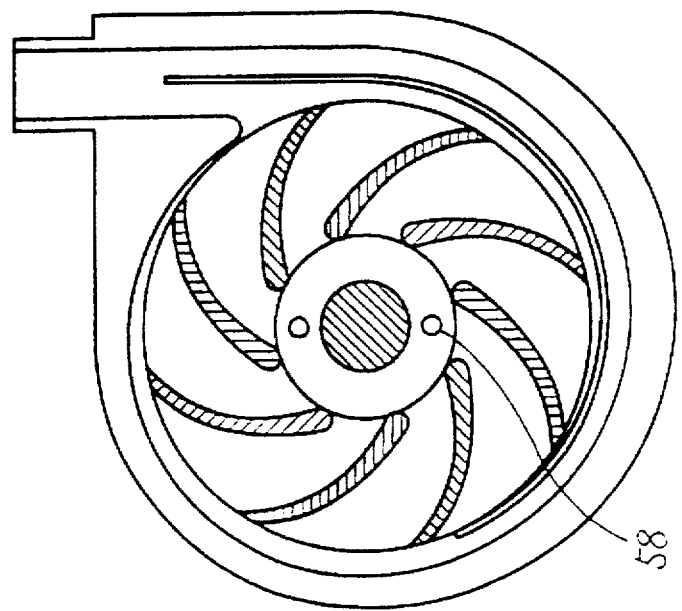
FIGS. 13A and 13B are cross sections showing a still further embodiment of a magnetically suspended type pump.
Figure 13A:
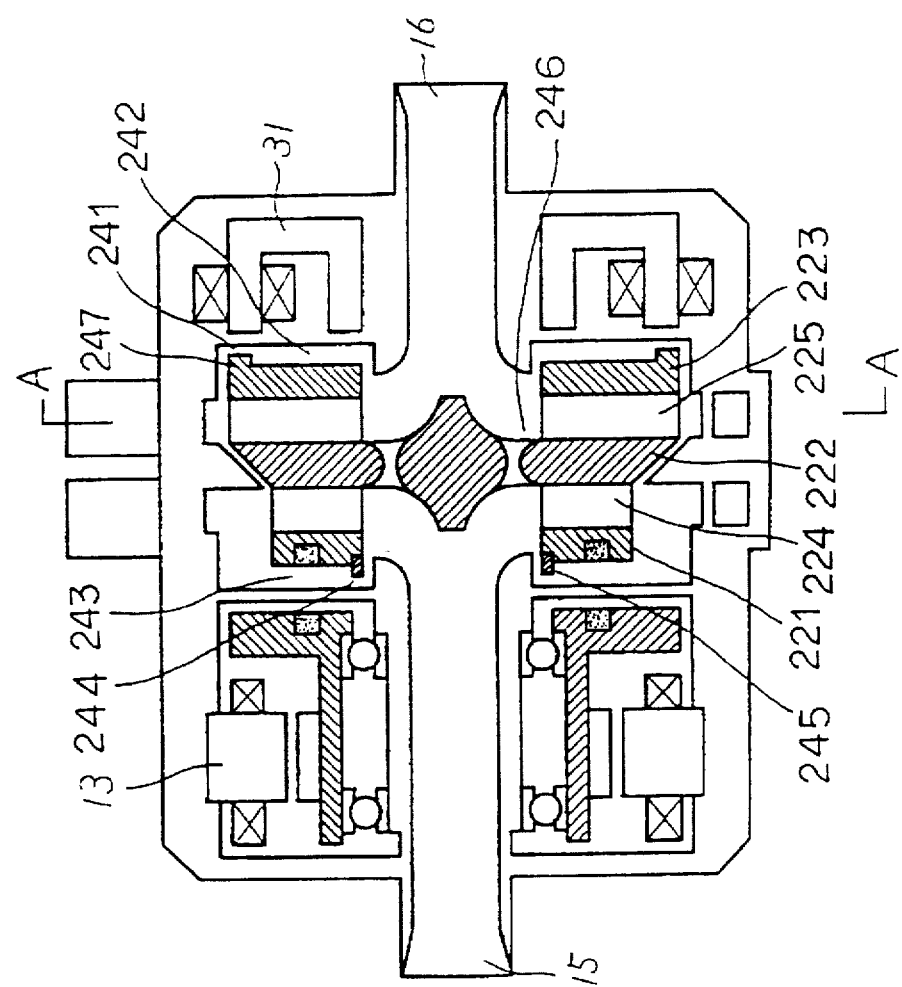

FIGS. 13A and 13B are cross sections showing a still further embodiment of a magnetically suspended type pump, wherein FIG. 13A is a sectional view and FIG. 13B is a cross section taken along the line A—A of FIG. 13A. In the example shown in FIGS. 13A and 13B, fluid pressure in the axial direction in the embodiment shown in FIGS. 11A and 11B is reduced. More specifically, in order to reduce fluid pressure in the axial direction, a ring-shaped projection 247 is formed in an outer diameter portion of a circular plate 223 such that a clearance 241 in an outer diameter portion of impeller 22 on the side of higher pressure is smaller than a clearance 242 in an inner diameter portion thereof. In addition, in order to make a clearance 243 in an outer diameter portion of impeller 22 on the side of lower pressure smaller than a clearance 244 in an inner diameter portion thereof, a projecting self-lubricant 245 with a ring shape is provided in the inner diameter portion of circular plate 221. Furthermore, a connection port 246 is formed so as to make the higher pressure side and the lower pressure side communicate with each other, and this connection port 246 functions to cause fluid to bypass lungs when balance of right and left hearts is lost due to malfunction of a living body.

Figure 14B:
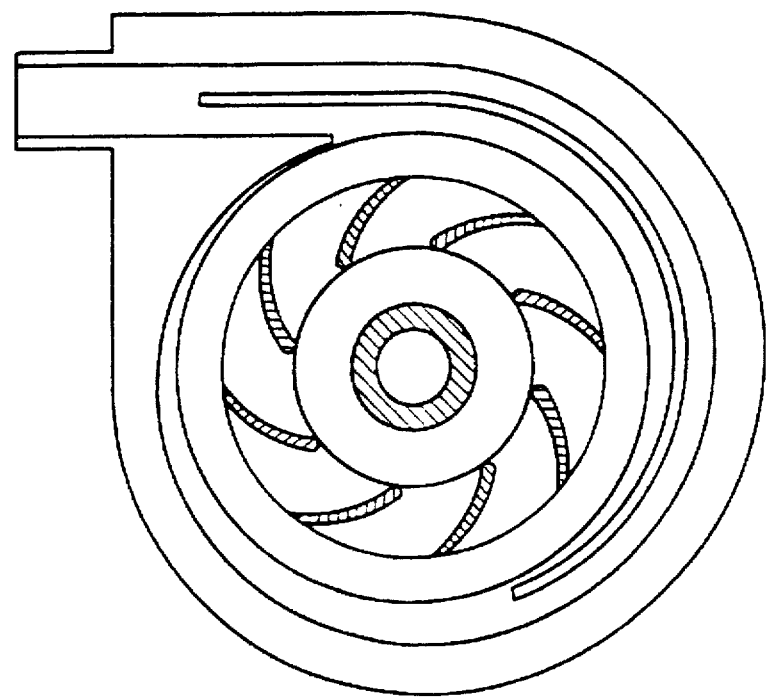
FIGS. 14A and 14B are cross sections showing a yet further embodiment of a magnetically suspended type pump.
Figure 14A:
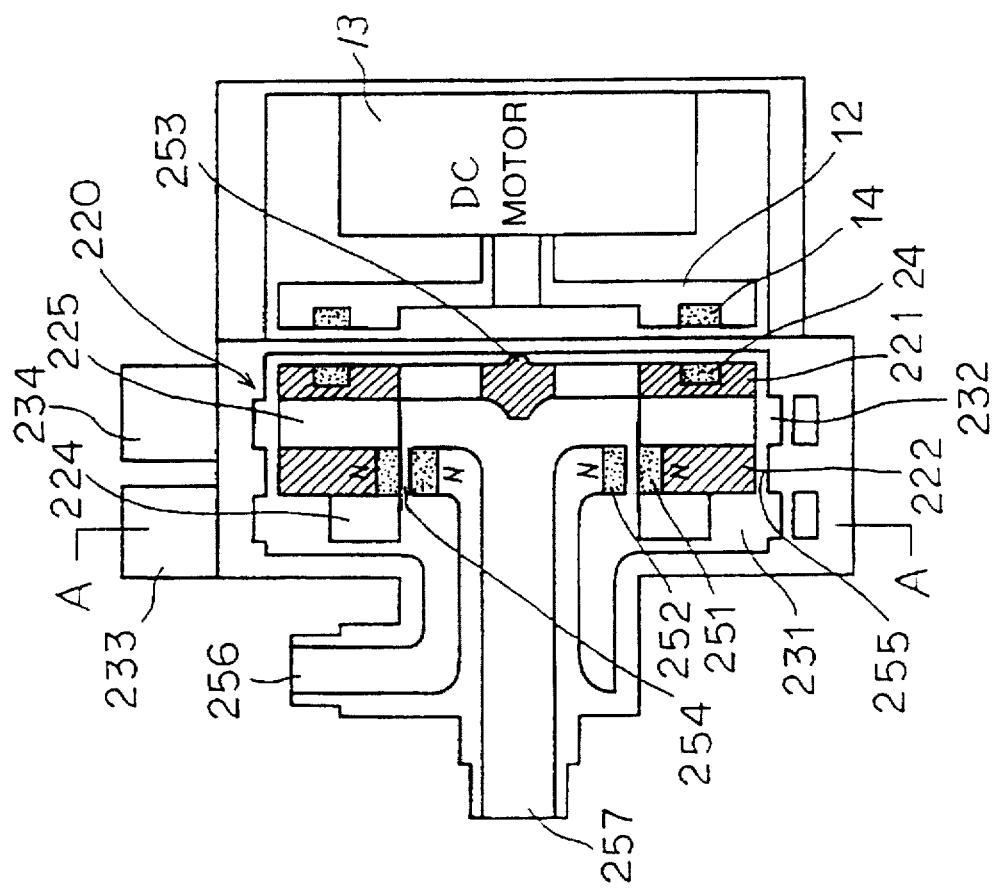
Figure 15:
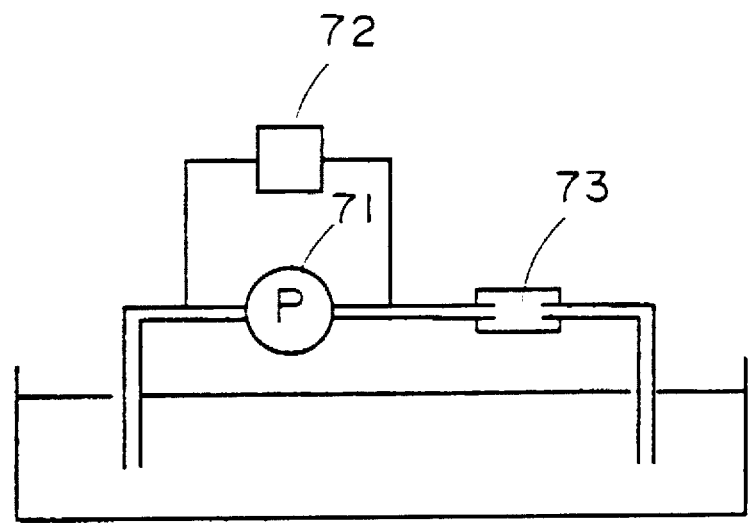
FIG. 15 is a diagram showing a conventional blood pump system.
Figure 16:
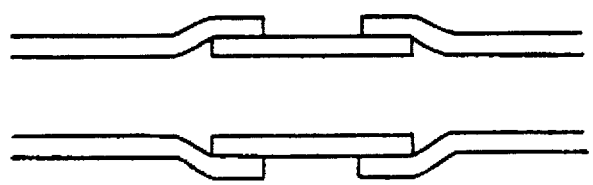
FIG. 16 is a diagram showing a conventional pump system in which thrombus formation occurs.

FIGS. 14A and 14B are cross sections showing a yet further embodiment of a magnetically suspended type pump, wherein FIG. 14A is a sectional view and FIG. 14B is a cross section taken along the line A—A of FIG. 14A. The impeller 22 is supported by a control type magnetic bearing and a non-control type magnetic bearing in the embodiments shown in FIGS. 11A and 11B and FIGS. 13A and 13B, while an impeller 220 is supported by two non-control type magnetic bearings in the embodiment shown in FIGS. 14A and 14B. More specifically, impeller 220 is constituted by two circular plates 221 and 222, and blades 225 and 224 respectively attached on the left sides of these circular plates 221 and 222. Permanent magnets 24 and 14 are respectively embedded in circular plate 221 and in a rotor 12 so as to have opposite polarities to each other, and constitute a first non-control type magnetic bearing. A permanent magnet 251 is attached on an inner diameter portion of circular plate 222, and a permanent magnet 252 is attached on a case so as to have a polarity opposite to that of this permanent magnet 251. These permanent magnets 251 and 252 radially repulsive to each other, and constitute a second non-control type radial magnetic bearing.

A pivot bearing 253 is put on the center of circular plate 221, and supports impeller 220 by coming in contact with the case. Blades 224 and 225 serve as pumps for right and left hearts, respectively, as in the case of the embodiments shown in FIGS. 11A and 13A. An inlet 256 for the right heart is formed to extend from a pump chamber 231 in the axial direction and to be bent outward at a right angle. An inlet 257 for the left heart is formed to extend outward along the axial direction of the central axis. In addition, two routes of flow path are labyrinth-sealed by clearances 254 and 255, respectively. In the present embodiment, impeller 220 is supported by magnetic bearing with attraction of permanent magnets 14 and 24 and repulsion of permanent magnets 251 and 252, impeller 220 is rotated by the driving force of motor 13, and blood sucked from inlet 256 is discharged through pump chamber 231 from an outlet 233 by rotation of blade 224. In addition, blood sucked from inlet 257 is discharged through pump chamber 232 from an outlet 234 by rotation of blade 225.

As described above, in the present embodiment, two blades are equipped coaxially in the impeller, and this impeller is supported within the case by magnetic bearing and is rotated by the driving force of the motor, whereby blood can be sucked from the inlets corresponding to the respective blades and can be discharged through the respective pump chambers from the respective outlets, resulting in reduction in size, cost and power consumption.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A magnetically suspended type pump in which an impeller is supported within a case by a magnetic bearing without contact and said impeller is rotated by a motor whose speed can be controlled by magnetic coupling through a partition therebetween, comprising:

processing means for obtaining a correlation between current flowing in said motor and fluid flow or between current flowing in said motor and outlet pressure;

control means for changing a speed of rotation of said motor based on the correlation between current and flow or between current and pressure obtained by said processing means, thereby controlling flow or pressure; and correction means for correcting flow or pressure obtained from blood viscosity which is obtained from disturbance response of said impeller supported by said magnetic bearing.

2. The magnetically suspended type pump in accordance with claim 1, further comprising:

disturbance signal generating means for generating a disturbance signal for periodically applying disturbance in order to measure said viscosity.

3. The magnetically suspended type pump in accordance with claim 2, wherein said disturbance signal generating means generates a disturbance signal having a frequency at which support rigidity of said impeller is smallest.

4. The magnetically suspended type pump in accordance with claim 2, further comprising:

a band pass filter for passing only a disturbance frequency therethrough to detect displacement in order to measure said viscosity.

5. The magnetically suspended type pump in accordance with claim 4, further comprising:

correction means for adding correction according to a speed of rotation in order to measure said viscosity.

6. The magnetically suspended type pump in accordance with claim 1, wherein said magnetic bearing includes a passive type magnetic bearing for radially supporting one side of said impeller, and a control type magnetic bearing for controlling an axial direction of said impeller on another side and controlling about two axes which are at right angles thereto.

7. The magnetically suspended type pump in accordance with claim 6, wherein said impeller includes a bypass port for making said lower pressure side and said higher pressure side communicate with each other.

8. A magnetically suspended type pump in which an impeller is supported within a case by a magnetic bearing without contact and said impeller is rotated by a motor whose speed can be controlled by magnetic coupling through a partition therebetween, comprising:

processing means for obtaining a correlation between current flowing in said motor and fluid flow or between current flowing in said motor and outlet pressure; and control means for changing a speed of rotation of said motor based on the correlation between current and flow or between current and pressure obtained by said processing means, thereby controlling flow or pressure, wherein said impeller includes two coaxial blades, and said case includes inlets, outlets and pump chambers which serve as flow paths for said two blades, respectively, said two blades are different in shape from each other so that said pump chambers have higher pressure or lower pressure at a fixed speed of rotation.

9. The magnetically suspended type pump in accordance with claim 8, wherein said impeller includes circular plates for separating said two blades from each other, and said pump further comprising:

a seal structure formed so as to seal space between said circular plate and said case and to have a diameter increased from a lower pressure side towards a higher pressure side.

10. The magnetically suspended type pump in accordance with claim 8, wherein said impeller includes a ring-shaped circular plate provided between said case and said blade located on the lower pressure side for rotating coaxially with the blade, and a self-lubricant provided on a side of an inner diameter of said ring-shaped circular plate for coming in contact with said case when said magnetic bearing malfunctions.

11. A magnetically suspended type pump in which an impeller is supported within a case by a magnetic bearing without contact and said impeller is rotated by a motor whose speed can be controlled by magnetic coupling through a partition therebetween, comprising:

processing means for obtaining a correlation between current flowing in said motor and fluid flow or between current flowing in said motor and outlet pressure; and control means for changing a speed of rotation of said motor based on the correlation between current and flow or between current and pressure obtained by said processing means, thereby controlling flow or pressure, wherein said magnetic bearing includes:

a first passive type magnetic bearing for radially supporting one side of said impeller, and a second passive type magnetic bearing having a pair of magnets located on another side of said impeller so as to radially repulsive to each other.

* * * * *